(12) United States Patent
Staud

(10) Patent No.: US 6,551,238 B2
(45) Date of Patent: Apr. 22, 2003

(54) PROTECTIVE TUBE FOR USE IN THE STERILIZATION OF FLEXIBLE ENDOSCOPES AND STERILIZATION METHOD

(75) Inventor: Ralf Staud, Emmingen (DE)

(73) Assignee: Karl Storz GmbH & Co. KG. (DE)

( * ) Notice: Subject to any disclaimer, the term of this patent is extended or adjusted under 35 U.S.C. 154(b) by 9 days.

(21) Appl. No.: 09/732,340

(22) Filed: Dec. 7, 2000

(65) Prior Publication Data

US 2001/0025133 A1 Sep. 27, 2001

Related U.S. Application Data

(63) Continuation of application No. PCT/EP00/02744, filed on Mar. 29, 2000.

(30) Foreign Application Priority Data

Apr. 8, 1999 (DE) .......................... 199 15 812

(51) Int. Cl.⁷ .............................................. A61B 1/00
(52) U.S. Cl. ...................................... 600/121; 600/133
(58) Field of Search ............................... 600/121, 133, 600/124, 125

(56) References Cited

U.S. PATENT DOCUMENTS 5,125,395 A * 6/1992 Adair .......................... 600/121
5,429,118 A * 7/1995 Cole et al. .................... 600/121
5,827,177 A * 10/1998 Oneda et al. ................. 600/121
5,868,667 A * 2/1999 Lin et al. ..................... 600/121
5,876,331 A * 3/1999 Wu et al. ..................... 600/133
5,916,145 A * 6/1999 Chu et al. .................... 600/121

FOREIGN PATENT DOCUMENTS

| DE | 3928532 A1 | 3/1991 |
| DE | 19749687 A1 | 5/1998 |
| EP | 0027185 A1 | 4/1981 |
| EP | 0744153 A1 | 11/1996 |

OTHER PUBLICATIONS

Pferde, Endoskopie In Der Tiermedizin, Aug. 1995.

* cited by examiner

Primary Examiner—Linda C. M. Dvorak
Assistant Examiner—Jocelyn Ram
(74) Attorney, Agent, or Firm—St. Onge Steward Johnston & Reens LLC

(57) ABSTRACT

A protective tube is provided for use in sterilizing flexible endoscopes in a vacuum method. Such flexible endoscopes comprise a flexible sleeve at a distal end portion. The diameter of the protective tube is selected such that the tube can be slipped onto and fit onto the distal end portion. The length of the tube is selected such that it at least covers the end portion with the flexible sleeve. In addition, the structure of the tube is selected such that the flexible sleeve is protected against swelling under vacuum conditions, at the same time however the sterilizing agent reaches between the outside of the sleeve and the applied protective tube.

6 Claims, 2 Drawing Sheets

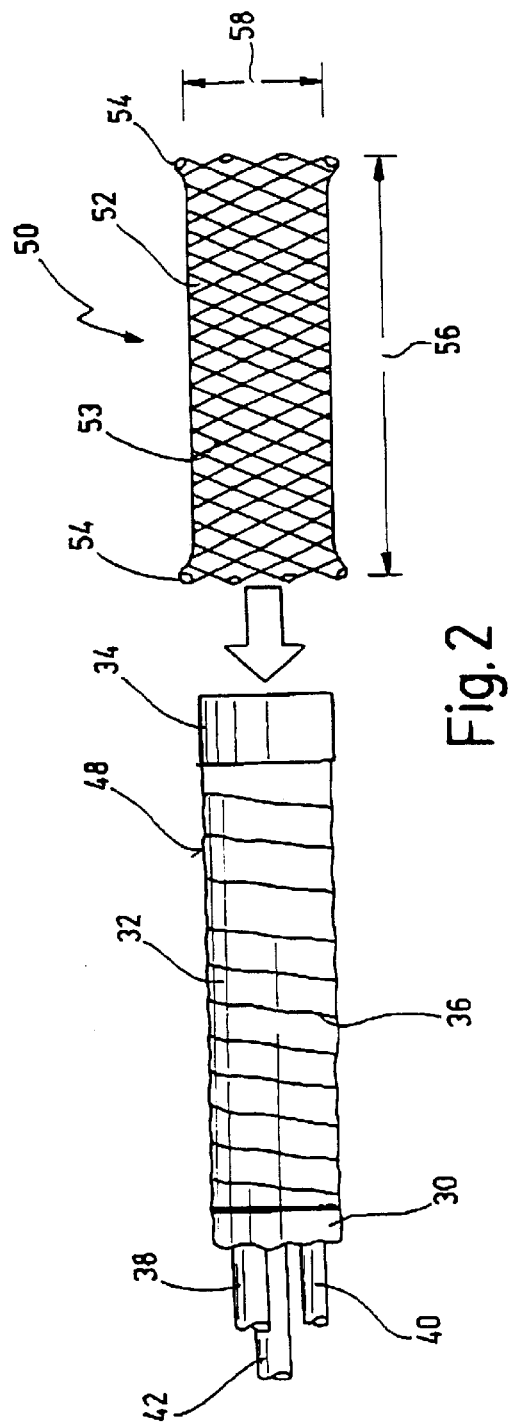
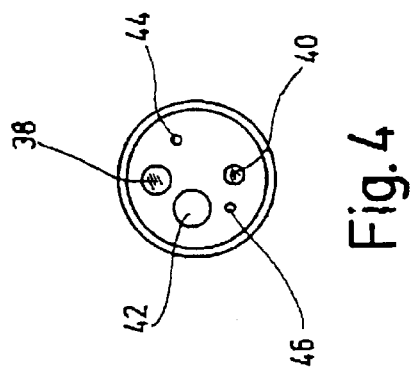
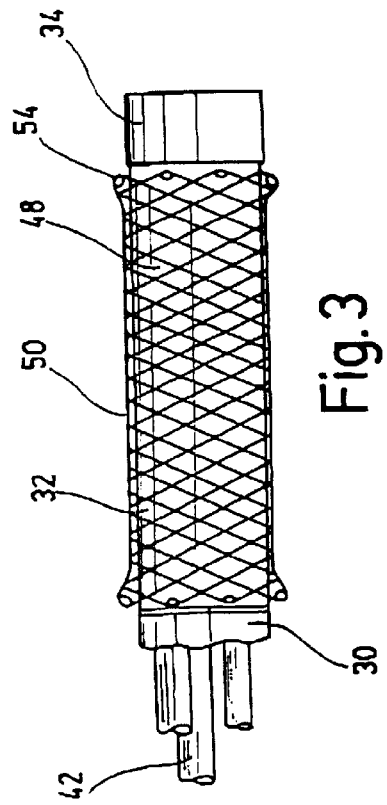

PROTECTIVE TUBE FOR USE IN THE STERILIZATION OF FLEXIBLE ENDOSCOPES AND STERILIZATION METHOD

CROSSREFERENCE OF PENDING APPLICATION

This application is a continuation of pending international application PCT/EP00/02744 filed on Mar. 29, 2000 which designates the US.

BACKGROUND OF THE INVENTION

The invention relates to a protective tube for use in the sterilization of flexible endoscopes in vacuum.

The invention further relates to an endoscope having such a protective tube thereon.

The invention still further relates to a sterilization method for sterilizating an endoscope having such a protective tube thereon.

Flexible endoscopes differ from rigid endoscopes in that the shaft has a flexibility such that it can be bent, strongly curved or even have a loop-like form. When the flexible endoscope is configured for operations and diagnostic procedures, it is used particularly for the stomach and intestines. Such a flexible endoscope for operations is disclosed in the German patent publication DE 39 28 532.

A broader use of such flexible endoscopes is in veterinary medicine, where they are used to investigate the upper and lower respiratory tracts and the air cells in horses. These endoscopes can also be used to investigate ulcers in the stomach or intestine and the entire urogenital tract of horses and other animals. The length of the flexible shaft in such applications is up to 2 meters.

Flexible endoscopes for veterinary medicine are disclosed for example in the catalog "Endoskopie in der Tiermedizin", 5$^{th}$ edition 1/95 from Karl Storz GmbH & Co., Tuttlingen, Germany. A 'Universal Fiberskop' with the article number 60309 VG is shown on page VET-H-FIB 3 in the catalog and comprises a headpiece from which a flexible shaft extends with a length of about 1 meter.

A distal end portion can be articulated even more extensively than the flexible shaft. This distal end portion can be bent or curved up to 220 degree with respect to the flexible shaft in a hook-like or semicircular arc-like manner. When the flexible shaft is inserted, for example past several turns in the intestinal tract, and then into a larger body cavity, for example the stomach, the distal end portion can be bent away from the longitudinal direction of the shaft by about 220 degrees in a circular arc and can also be rotated to the left or right by 90 degrees. In effect a complete panorama view of the region of the distal end is possible. To be able to perform these manipulations at the distal end portion of the shaft, it is provided with a particularly flexible sleeve which has the appearance of a rubber tube.

The covering of the flexible shaft in the remaining sections is relatively more rigid and has the appearance of a flexible plastic tube.

Thus the shaft on the whole is a flexible hollow pipe of tube-like form with several channels disposed in its interior, for example an instrument channel, several optical fiber channels, an image transmission channel with an objective at the end, a channel for cleaning and washing the objective and for example an insufflation channel. A rigid end piece is provided at the distal end face, which supports the distal ends of these various channels. The distal end portion with the particularly flexible rubber-like sleeve lies between this end piece and the longer flexible shaft.

A common technique for sterilization of such flexible endoscopes is to subject the endoscope to a vacuum in a closed space, where at the same time aggressive and microbiozidal media, for example hydrogen peroxide containing media, are employed as a sterilization agent.

In practice it has been found that the flexible sleeve at the distal end portion tends to swell and sometimes burst under vacuum. A pressure compensating cap is provided for venting the interior of the shaft during sterilization to allow pressure compensation between the interior of the shaft and the vacuum in the sterilization apparatus. The cap is provided on a special connector or at the head end, which is in communication with the interior of the shaft. Such a pressure compensating cap is shown on page VET-H-FIB 5 in the above-mentioned catalog with the article number 60025 E.

This pressure compensating cap comprises a valve through which air can escape from the interior of the shaft when a vacuum is applied to thereby provide pressure compensation. In practice it has been found that the aggressive sterilization agents can penetrate through the valve into the interior of the endoscope and can damage the components in the flexible shaft, in particular the sensitive optical equipment.

Instead of the compensating cap, other solutions have been attempted with a pressure compensating container. The amount of air drawn out of the interior of the endoscope when placed under vacuum is fed to the container and then flows back to the container when the vacuum is released. This however is very complicated in its construction.

The provision of a pressure compensating cap itself is complicated, but is necessary since otherwise the danger of leaks arise in the region of the distal end portion even after only a few sterilization cycles.

The object of the present invention is therefore to provide means which allow sterilization in the vacuum method and which ensure with constructively simple means that the flexible sleeve of the distal end portion is not damaged and no leaks arise.

SUMMARY OF THE INVENTION

According to the present invention, a protective tube is provided whose diameter is selected such that the tube fits to the distal end portion and can be slipped thereon. Its length is selected such that it at least covers the end portion having the flexible sleeve. The structure of the protective tube is such that the flexible sleeve is protected against swelling under vacuum conditions, where however the sterilizing agent can enter into the region between the outside of the sleeve and the mounted protective tube.

The protective tube is configured such that it acts as a type of support tube which protects the flexible sleeve of the distal end portion from inflating or swelling and therefore also against bursting. At the same time, its structure is partially open, i.e. is selected such that the sterilizing agent can reach between the protective tube and the outside of the sleeve, so that this region can also be thoroughly sterilized. The tube can be simply slipped onto the distal end portion before sterilization due to the selection of its corresponding diameter and also sits on the end portion so as not to fall off during corresponding handling procedures. By selecting the corresponding length, it is ensured that the entire length of the distal end portion, which is provided with such a flexible sleeve, does not swell and therefore burst when vacuum is applied.

Thus a protection of this critical region is provided against swelling, bursting and leakage with simple mechanical means. A further considerable advantage is that the interior of the endoscope or the shaft can be formed as a closed system against the sterilizing agent, such that no communication with the sterilizing environment exists, for example through valve openings or the like. It is thus excluded that the aggressive agents can enter into the interior. The selection of material for the protective tube to allow sufficient stability and to allow passage of the agents is easy to carry out and is adapted to the respective constructive features of the flexible endoscope.

In this manner, the object is completely achieved.

In an embodiment of the present invention, the structure of the protective tube is a fabric. This has the advantage that the textile or fabric configuration is very simple to fabricate and provides a stable but filigree netting with sufficient openings for passage of the sterilizing agent. The agent can reach the entire outer side of the sleeve of the distal end portion, over which the protective tube has been placed. In addition, such fabric structures are inexpensive to produce, so that such a protective tube can be formed as a one-use throwaway article.

In a further embodiment of the present invention, the protective tube comprises a flaring at at least one end. This feature has the advantage that the widened end helps to introduce the distal end portion into the protective tube or conversely to slide the protective tube onto the distal end portion of the flexible endoscope. Not only can the protective tube be slipped on in a simple manner, it is also guaranteed that the tube is not damaged and can be applied to be fully functional.

In a further embodiment of the present invention, the fabric is composed of fibers intertwined in spiral lines. The structure is similar to that of a reinforcing fabric, which is common in high pressure hoses, which is very simple to manufacture. On the other hand, a very reliable protection is provided against a swelling of the sleeve, even at low vacuums, so that even an inadvertent malfunction of the sterilizing chamber causing excessive vacuum is not harmful. Even in this case, the sleeve of the distal end portion is protected against being inflated or bursting.

The protective tube can be applied directly after manufacture and before the first sterilization procedure. It can remain on the end portion, which indicates to the user that this endoscope has been sterilized. This can also be performed for subsequent sterilization cycles, i.e. the protective tube can initially remain on the end portion after sterilization, so that an additional protection against mechanical disturbances is present and the protective tube is drawn off only just before use. The tube thus not only fulfills a function during the actual sterilization procedure, but also subsequently a protective function and at the same time an information function. The user is informed that the endoscope has actually been sterilized. Thus the invention also includes the combination of a flexible endoscope having a protective tube slipped onto its distal end portion.

A method for sterilizing a flexible endoscope under vacuum then comprises sliding a protective tube with the above-described features onto the distal end portion of an endoscope and performing sterilization under vacuum of the assembly comprising the endoscope and protective tube. Depending on the preference of the manufacturer or user, the protective tube can be removed immediately after sterilization or be pulled off just before use.

It will be understood that the above-mentioned features and those to be discussed below are not only applicable in the given combinations, but may also be used in other combinations or taken alone without departing from the scope of the present invention.

BRIEF DESCRIPTION OF THE DRAWINGS

The invention will be described in more detail below in conjunction with a selected embodiment.

FIG. 2 shows an enlarged illustration of the distal end portion of the flexible endoscope of FIG. 1 in straight alignment and a protective tube according to the present invention, which is to be slid onto the distal end portion.

FIG. 3 shows an illustration similar to FIG. 2 of the distal end portion of the flexible endoscope after the protective tube has been slipped on.

FIG. 4 shows a view of the end face of the distal end of the flexible endoscope of FIG. 1.

DETAILED DESCRIPTION OF A PREFERRED EMBODIMENT

Figure 1:
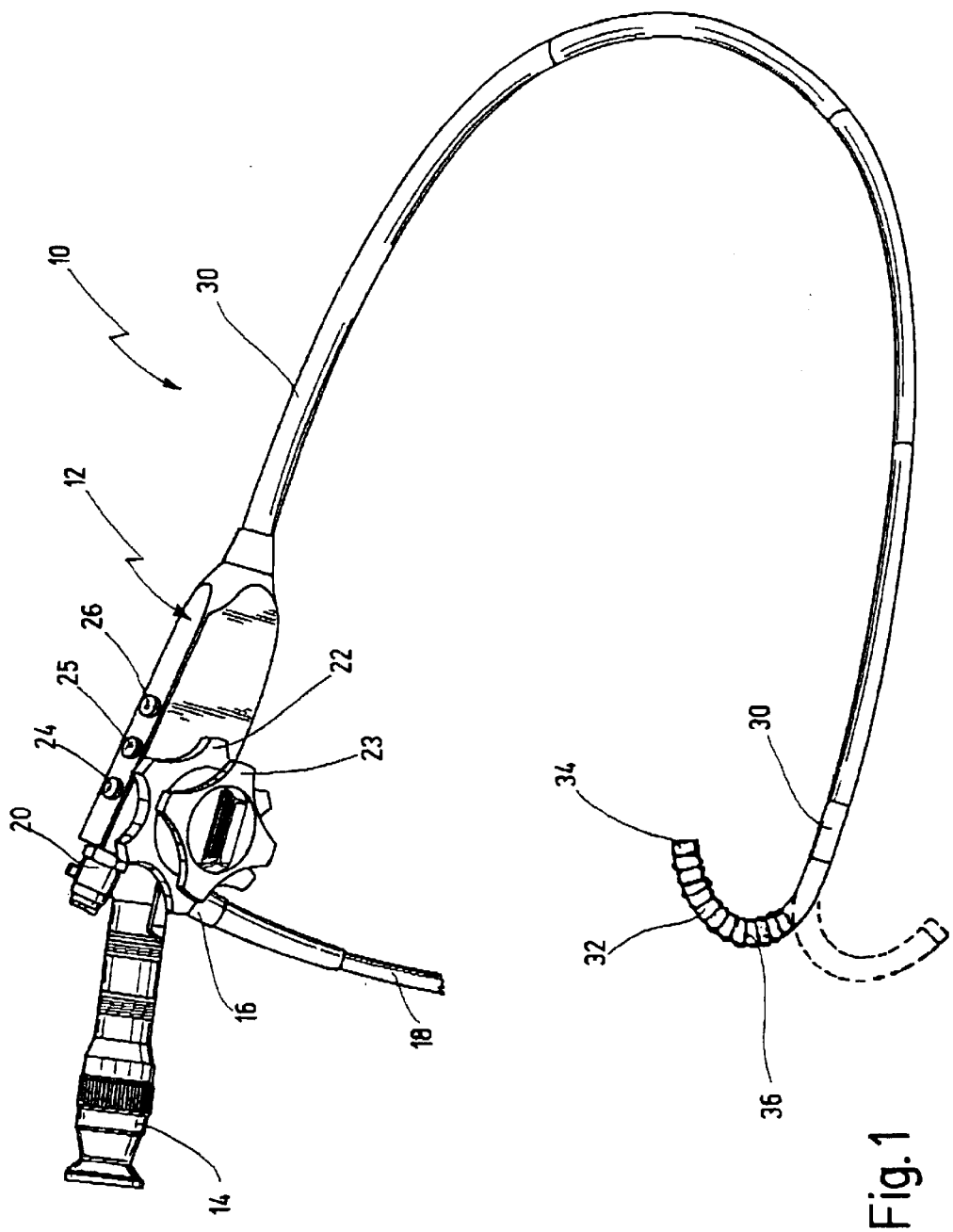
FIG. 1 shows a perspective view of a flexible endoscope having a distal end portion with a particularly flexible sleeve.

A flexible endoscope is illustrated in FIG. 1 and generally designated with the numeral 10. The flexible endoscope 10 comprises a headpiece generally indicated with the numeral 12.

An ocular 14 projects from the proximal side of the headpiece 12. A connector 16 projecting from the side is provided for connecting a train 18 of lines for illumination, flushing, insufflation, suctioning and the like. A further connector 20, extending approximately in the direction of the ocular 14, is provided for inserting pincers, slings, or the like in addition to the above instruments into the endoscope or into the headpiece 12.

Two hand wheels 22, 23 are provided at the side of the headpiece, whose function will be described below. In addition, switches 24, 25, 26 are arranged in the region of the head-piece 12, through which various functions are controlled, for example suctioning, flushing or the like, which is known per se in the configuration of flexible endoscopes.

The headpiece 12 continues into an elongated flexible shaft 30, which in the illustrated embodiment has a length of about 1 meter. The shaft 30 is made of a relatively rigid, but flexible plastic material, which allows a bending of the shaft 30 as illustrated in FIG. 1. Compared to the shaft 30, an end portion 32 has increased flexibility such that this end portion 32 can additionally be bent up to 180 degrees to form a semicircular shape as can be seen in FIG. 1. This end portion 32 can be rotated by means of a traction cable mechanism extending from the end piece 34 to the hand wheels 22, 23.

The end piece can be rotated by 180 degrees in a plane, the orientation of the shaft 30 remaining fixed, from the position illustrated in FIG. 1 with the solid lines to the position in FIG. 1 indicated with the dashed lines. In addition, it is also possible to move the bent end portion 32 starting from any disposition by about 90 degrees to the left or to the right, as is known per se. To allow the shaft 30 to undergo this extreme bending motion, the region of the end portion 32 is provided with a relatively soft, elastic, rubber-like sleeve 36. This configuration allows the extreme movements to be followed with the corresponding expansion in the outer region of the radius of curvature or the corresponding contraction at the inner region of the radius of curvature.

As can be seen from the plan view in FIG. 4, a metal end piece 34 is provided at the distal side, where the corresponding channels or components end, i.e. an image transmission element 38, an optical fiber 40, an instrument channel 42 and components of the drive mechanism, for example the cables 44 and 46.

The interior of the tubular shaft 30 is sealingly closed against the outside at the distal end by the end piece 34 and at the proximal end by the headpiece 12. In the conventional vacuum sterilization method, the danger exists that the shaft 30 can swell and burst in the region of the flexible sleeve 36 of the end portion 32, so that leaks can arise.

This is now prevented by the protective tube 50 of the present invention as shown in FIG. 2. The protective tube 50 has the form of a section of a tube i.e. has a tubular body, whose structure 52 comprises openings. This is accomplished in that the structure, i.e. the tube wall of the protective tube 50, is formed of a fabric 53. The fabric 53 consists of intertwined spiral-shaped fibers, the ends of which are expanded in a trumpet-shaped flaring 54.

The length 56 of the tube 50 is selected such that it covers the entire end portion 32 of the shaft 30. Depending on the length of the end portion 32, one single protective tube 50 or several such tubes can be slipped on one after another. If the shaft 30 is formed of such a soft flexible material over its entire length, so that swellings and a bursting could be expected under vacuum, then self-evidently a correspondingly longer protective tube 50 or several tubes can be applied.

The diameter 58 of the tube 50 is selected such that its clearance inner diameter corresponds approximately to the clearance outer diameter of the end portion 32. Especially in conjunction with the flarings 54, this guarantees that the protective tube 50 can be simply and securely slipped over the end piece 34 and onto the end portion 32 and is seated there by friction so as not to fall off. This situation is illustrated in FIG. 3.

The fabric-like structure 52 provides sufficient stability against swelling of the sleeve 36 when vacuum is applied, thereby preventing swelling and leakage of the shaft 30. Due to the frictional fit, the protective tube 50 can be applied before placing the endoscope in the corresponding autoclave and the corresponding manipulations can be carried out subsequently, without the protective tube 50 releasing from the end portion 32.

The fabric-like structure 52 with holes ensures that a corresponding liquid or gaseous sterilizing agent can reach between the protective tube 50 and the outside 48 of the end portion 32, namely over the entire surface of the outside 48, also in the regions of the fibers of the fabric 53. This then ensures that the entire outer side 48 comes into contact with the sterilizing agent and is sterilized.

After performing the sterilization procedure, the protective tube 50 can remain in position and then only be removed when the flexible endoscope is to be used again. The protective tube 50 however can also be removed immediately, depending on the user's preference. Since the tube 50 is evidently also sterilized in the sterilization procedure, it can also be used again or be thrown away after a single use. Plastic fiber materials can be employed, which are resistant against aggressive hydrogen peroxide containing sterilizing agents, such as those known under the trademark-protected names TREVIRA or TYVEK.

In the above embodiment, the protective tube 50 was provided with extra trumpet-like flarings 54. It is also possible to form the end piece 34 to be slightly conical, so that the protective tube 50 can be formed strictly geometrically as a cylinder, which is easier to manufacture, so that the conical configuration of the end piece 34 aids in sliding on the tube or inserting the end portion.

Flexible endoscopes of the applicant were tested, which have the article numbers 11001BC, 11272C, 13309, 13308A and which have shaft diameters of 4 mm, 9 mm and 11 mm. The flexible end region was protected with a fabric tube made of TREVIRA and subjected to a pressure change 1,350 times. The pressure changes correspond to that in a vacuum sterilization procedure.

After this large number of pressure changes, no leakage could be found in the region of the sleeve 36, i.e. after this large number of loading phases no pressure drop could be determined after ten minutes, which was larger than the pressure drop observed before this number of test cycles.

These pressure cycles could be simulated, such that the interior of the shaft 30 is supplied with a pressure corresponding to the pressure difference to the outside, which arises in a sterilization device when a corresponding vacuum is applied.

This demonstrates that the sealing properties in the region of the end portion 32 can be maintained by the mechanically simple measure of sliding on the protective tube 50 with the fabric-like structure 52.

What is claimed is:

1. A protective tube adapted to be slipped on a distal end portion of a flexible endoscope prior to a vacuum sterilization method and adapted to be removed from said distal end portion after sterilization prior to a consecutive use of said flexible endoscope, said protective tube having
   a tubular body,
   a diameter of said protective tube is selected such that said protective tube can be slipped onto said distal end portion of said flexible endoscope and fits onto said distal end portion,
   a length of said protective tube being selected such that it covers at least said end portion of said flexible endoscope with said flexible endoscope, and
   a structure of said body of said protective tube being selected such that said flexible sleeve is protected under vacuum condition against expanding, a sterilizing agent used during sterilizing of said flexible endoscope is able to penetrate between an outside of said sleeve and said protective tube applied onto said sleeve.

2. The protective tube of claim 1, wherein said structure of said tubular body is a textile or a fabric construction.

3. The protective tube of claim 2, wherein said structure is formed of spiral line shaped intertwined fibers.

4. The protective tube of claim 1, wherein said tubular body is provided with a flaring on at least one end thereof.

5. An assembly of a flexible endoscope and a protective tube slipped onto a distal end portion of said flexible endoscope for performing a vacuum sterilization method, said flexible endoscope having a headpiece and a shaft having a flexible sleeve at a distal end portion thereof, said protective tube having
   a tubular body,
   a diameter of said protective tube is selected such that said protective tube can be slipped onto said distal end portion of said flexible endoscope and fits onto said distal end portion,
   a length of said protective tube being selected such that it covers at least said end portion of said flexible endoscope with said flexible sleeve, and
   a structure of said body of said protective tube being selected such that said flexible sleeve is protected under vacuum condition against expanding, a sterilizing agent used during sterilizing of said flexible endoscope is able to penetrate between an outside of said sleeve and said protective tube applied onto said sleeve.

6. A method for sterilizing a flexible endoscope in a vacuum method, comprising the steps of slipping on a protective tube on a distal end portion of a flexible endoscope whose shaft comprises a flexible endoscope, said protective tube having a tubular body, a diameter of said protective tube is selected such that said protective tube can be slipped onto said distal end portion of said flexible endoscope and fits onto said distal end portion, a length of said protective tube being selected such that it covers at least said end portion of said flexible endoscope with said flexible sleeve, and a structure of said body of said protective tube being selected such that said flexible sleeve is protected under vacuum condition against swelling, a sterilizing agent used during sterilizing of said flexible endoscope is able to penetrate between an outside of said sleeve and said protective tube applied onto said sleeve, performing a vacuum sterilization procedure with said assembly of said flexible endoscope and said protective tube applied thereon, and removing said protective tube before using the endoscope.

* * * * *